(12) United States Patent
Endo et al.

(10) Patent No.: US 10,590,141 B2
(45) Date of Patent: Mar. 17, 2020

(54) THIOGLYCOLURIL COMPOUND, AND METHOD FOR PRODUCING SAME

(71) Applicant: NISSAN CHEMICAL CORPORATION, Tokyo (JP)

(72) Inventors: Masahisa Endo, Toyama (JP); Gun Son, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/330,071

(22) PCT Filed: Aug. 22, 2017

(86) PCT No.: PCT/JP2017/029980
§ 371 (c)(1),
(2) Date: Mar. 1, 2019

(87) PCT Pub. No.: WO2018/043215
PCT Pub. Date: Mar. 8, 2018

(65) Prior Publication Data
US 2019/0225619 A1 Jul. 25, 2019

(30) Foreign Application Priority Data
Sep. 2, 2016 (JP) ................... 2016-171647

(51) Int. Cl.
*C07D 487/04* (2006.01)
(52) U.S. Cl.
CPC .................. *C07D 487/04* (2013.01)
(58) Field of Classification Search
CPC .................................................. C07D 487/04
See application file for complete search history.

(56) References Cited

FOREIGN PATENT DOCUMENTS

| JP | H05-262772 A | 10/1993 |
| JP | 3154819 B2 | 4/2001 |
| JP | 2013-033276 A | 2/2013 |
| WO | 2009/096340 A1 | 8/2009 |

OTHER PUBLICATIONS

Oct. 10, 2017 International Search Report issued in International Patent Application No. PCT/JP2017/029980.
Oct. 10, 2017 Written Opinion issued in International Patent Application No. PCT/JP2017/029980.
Mandeep Singh et al. "The Synthetic Challenge of Thioglycolurils". European Journal of Organic Chemistry, 2014, pp. 933-940.
Christopher N. Cow et al. "A Facile Preparation of Thioglycolurils From Glycolurils, and Regioselectivity in Thioglycoluril Template-Directed Crossed-Claisen Condensations". Journal of Organic Chemistry, 1997, vol. 62, pp. 8834-8840.
Mandeep Singh et al. "Dual-Functional Semithiobambusurils". Chemistry A European Journal, 2015, vol. 21, pp. 536-540.
Vladimir V. Baranov et al. "New Access to Thioglycolurils by Condensation of 4,5-Dihydroxyimidazolidin-2-Ones(Thiones) With HSCN". Tetrahedron Letters, 2015, vol. 56, pp. 6085-6088.

*Primary Examiner* — Golam M Shameem
(74) *Attorney, Agent, or Firm* — Oliff PLC

(57) ABSTRACT

A novel monothioglycoluril compound and a novel dithioglycoluril compound. A thioglycoluril compound of the following Formula (1):

(wherein X is an oxygen atom or a sulfur atom, and four Rs are each a hydrogen atom, a linear, branched, or cyclic alkyl group having a carbon atom number of 1 to 4, a phenyl group, a naphthyl group, a benzyl group, or a $C_{3-9}$ alkyl group having at least one ether bond on the main chain).

3 Claims, 2 Drawing Sheets

[Fig.1]
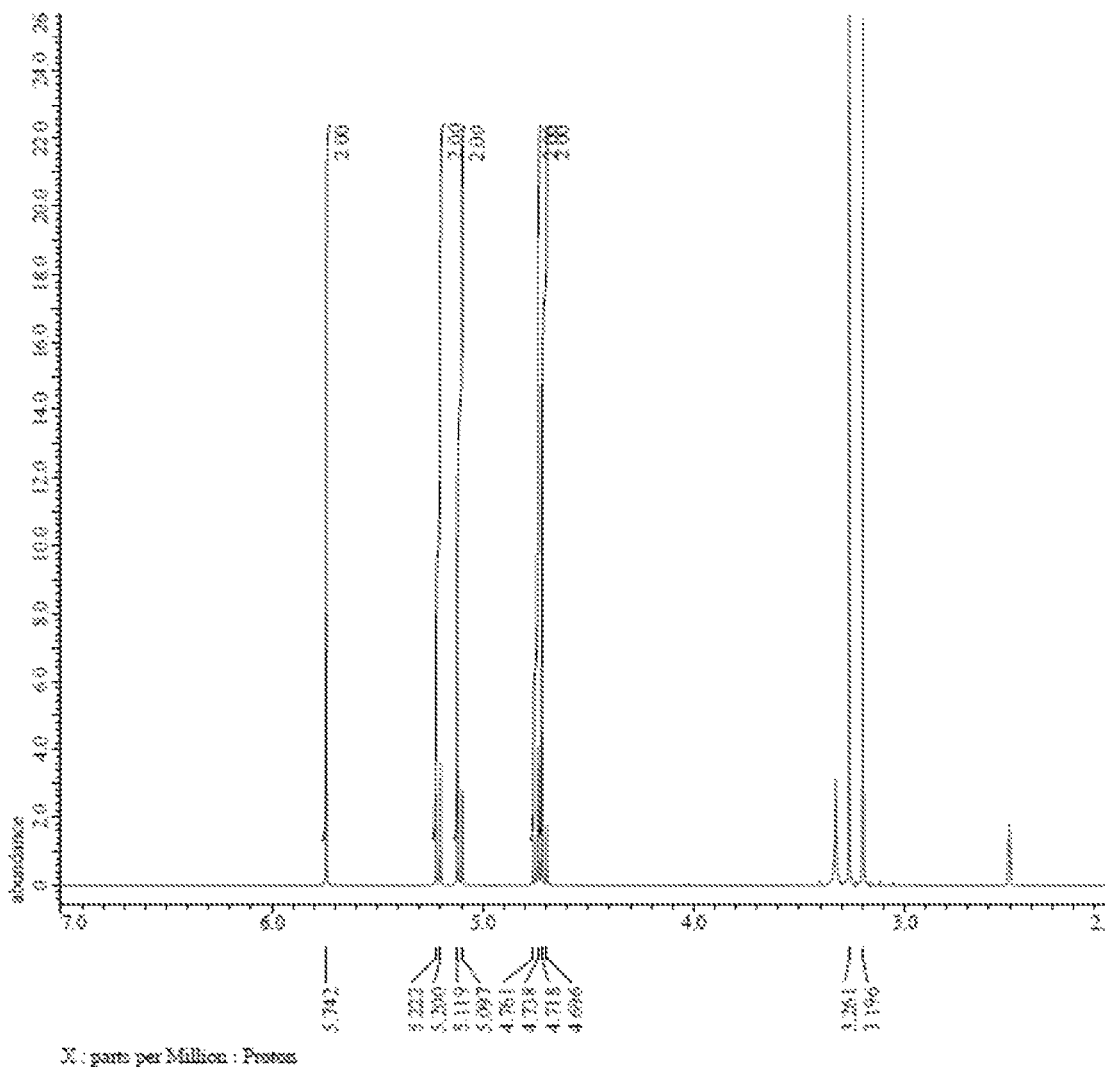

[Fig.2]
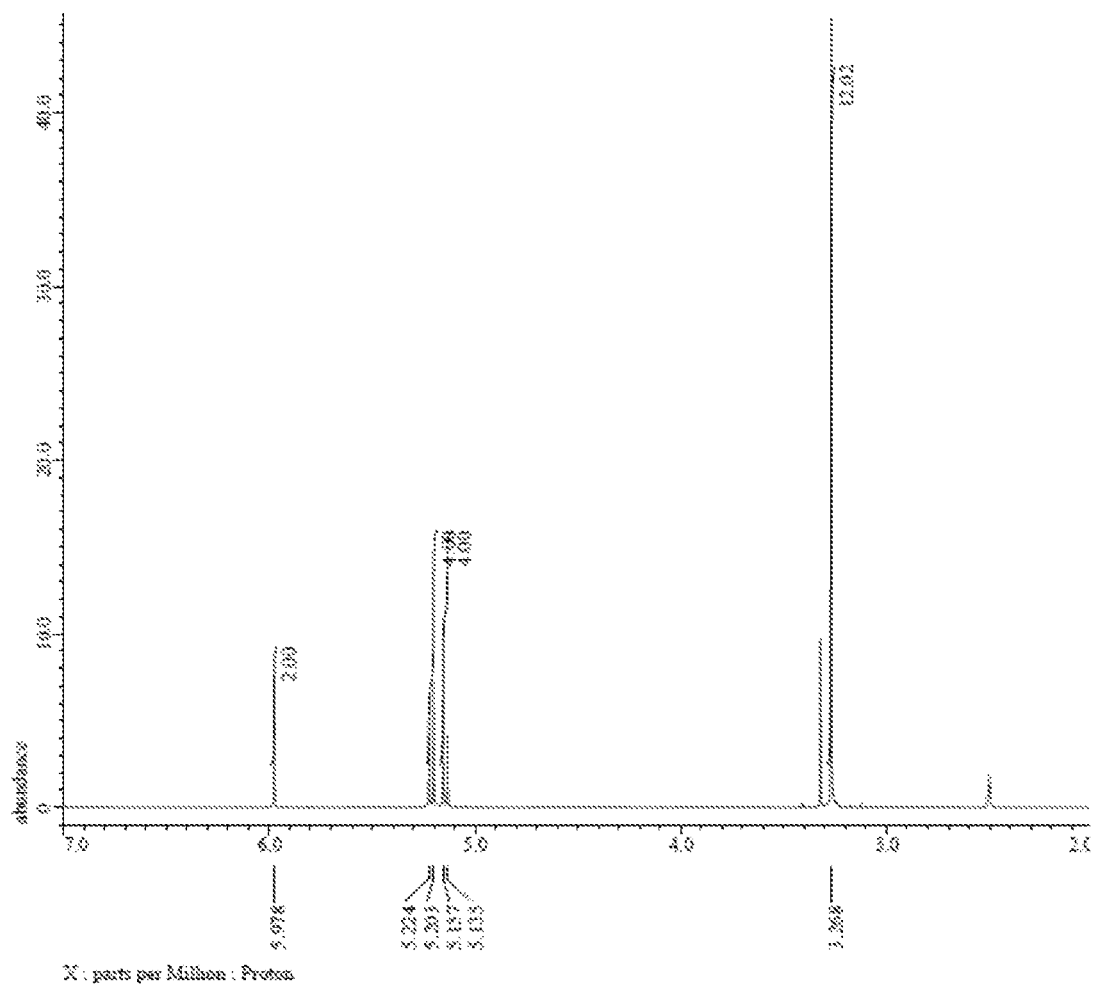
[Fig.3]
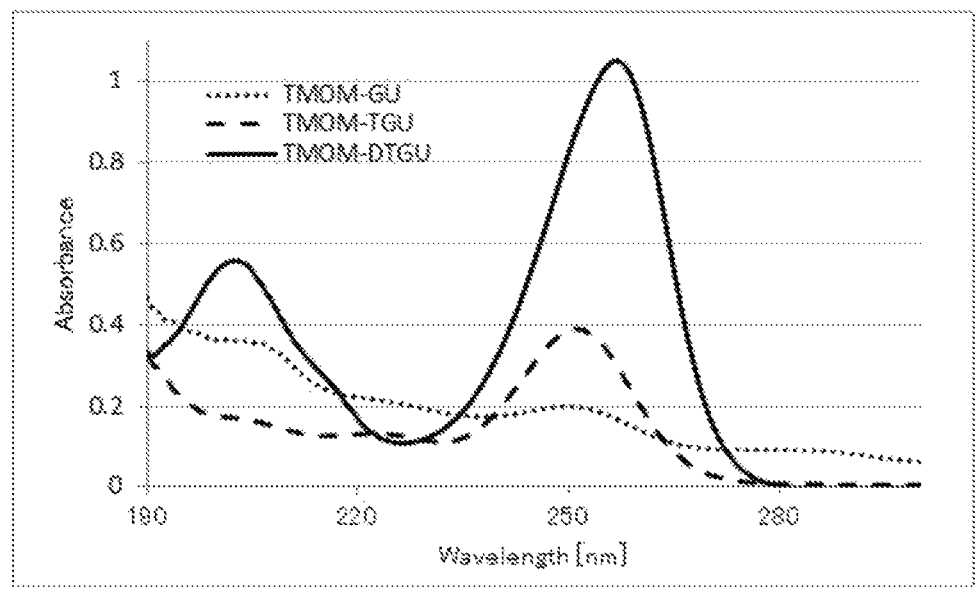

THIOGLYCOLURIL COMPOUND, AND METHOD FOR PRODUCING SAME

TECHNICAL FIELD

The present invention relates to a novel monothioglycoluril compound and a novel dithioglycoluril compound, and methods for producing these compounds.

BACKGROUND ART

Glycoluril compounds are heterocyclic compounds each having four urea nitrogen atoms in the ring structure. Glycoluril compounds having various substituents on the urea nitrogen atoms have been produced and used as functional compounds.

For example, 1,3,4,6-tetrakis(methoxymethyl)glycoluril, which has four methoxymethyl groups in the molecule, is well known as a crosslinking agent for epoxy resins (see Patent Document 1).

A glycoluril compound prepared by substitution of an oxygen atom with a sulfur atom in the ring structure, for example, a monothioglycoluril compound and a dithioglycoluril compound, have also been known. A monothioglycoluril compound and a dithioglycoluril compound having substituents on a urea nitrogen atom or a thiourea nitrogen atom and on a bridgehead carbon atom have been synthesized (see Non-Patent Documents 1, 2, 3, and 4).

For example, Patent Document 2 discloses a method involving introduction of four methoxymethyl groups in one glycoluril molecule having no substituent. However, none of Patent Documents 1 and 2 and Non-Patent Documents 1, 2, 3, and 4 describes a monothioglycoluril compound and a dithioglycoluril compound in which the hydrogen atom on at least one nitrogen atom is substituted with an alkoxymethyl group such as a methoxymethyl group.

PRIOR ART DOCUMENTS

Patent Documents

Patent Document 1: Japanese Patent Application Publication No. 2013-33276 (JP 2013-33276 A)
Patent Document 2: Japanese Patent No. 3154819

Non-Patent Documents

Non-Patent Document 1: European journal of Organic Chemistry, pp. 933-940 (2014)
Non-Patent Document 2: Journal of Organic Chemistry, 62, 8834-8840 (1997)
Non-Patent Document 3: Chemistry A European Journal, 21, 536-540 (2015)
Non-Patent Document 4: Tetrahedron Letters, 56, 6085-6088 (2015)

SUMMARY OF THE INVENTION

Problems to be Solved by the Invention

A monothioglycoluril or dithioglycoluril compound having a plurality of alkoxymethyl groups in the molecule (e.g., two or more alkoxymethyl groups in the molecule) is useful as, for example, a crosslinking agent for epoxy resins. A monothioglycoluril or dithioglycoluril compound, which is prepared by substitution of at least one of two oxygen atoms with a sulfur atom in the ring structure of a glycoluril compound, has optical properties different from those of 1,3,4,6-tetrakis(methoxymethyl)glycoluril. In particular, a monothioglycoluril compound, in which only one of the aforementioned two oxygen atoms is substituted with a sulfur atom, is expected to have excellent solubility in a solvent because of its low molecular symmetry.

The present invention has been made on the basis of the situation described above, and an object of the present invention is to provide a novel monothioglycoluril compound and a novel dithioglycoluril compound.

Means for Solving the Problems

An aspect of the present invention is a thioglycoluril compound of the following Formula (1):

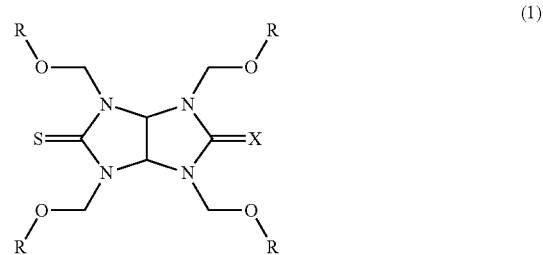

(wherein X is an oxygen atom or a sulfur atom, and four Rs are each a hydrogen atom, a linear, branched, or cyclic alkyl group having a carbon atom number of 1 to 4, a phenyl group, a naphthyl group, a benzyl group, or a $C_{3-9}$ alkyl group having at least one ether bond on the main chain).

The thioglycoluril compound of Formula (1) is a monothioglycoluril compound of the following Formula (2):

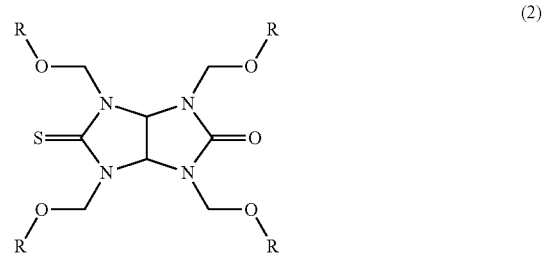

(wherein four Rs have the same meanings as defined above in Formula (1)).

The thioglycoluril compound of Formula (1) is a dithioglycoluril compound of the following Formula (3);

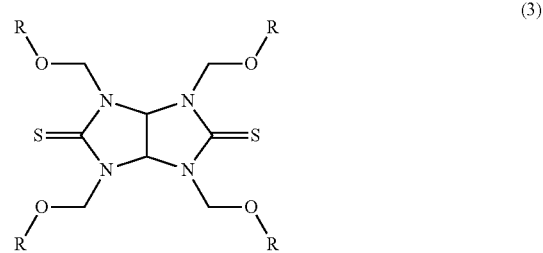

(wherein four Rs have the same meanings as defined above in Formula (1)).

Another aspect of the present invention is a method for producing a monothioglycoluril compound, the method comprising a first step of causing a reaction between formaldehyde and a compound of the following Formula (4a) in a basic aqueous solution, and then isolating a compound of the following Formula (2a) and a second step of causing a reaction between the compound of the following Formula (2a) and an alcohol of the following Formula (5) in an acidic solution containing the alcohol as a solvent, adding a basic aqueous solution to the resultant reaction mixture, and purifying the resultant product by silica gel column chromatography for removal of impurities from the product, so as to produce a monothioglycoluril compound of the following Formula (2b):

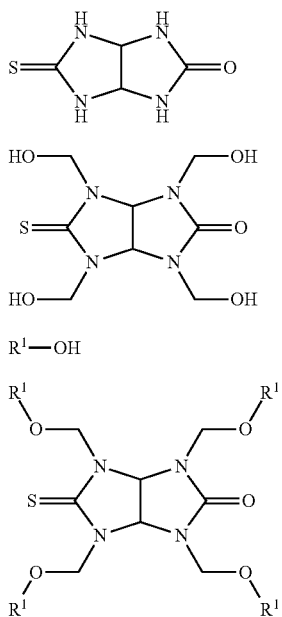

(4a)

(2a)

(5)

(2b)

(wherein four $R^1$s are each a linear, branched, or cyclic alkyl group having a carbon atom number of 1 to 4, a phenyl group, a naphthyl group, a benzyl group, or a $C_{3-9}$ alkyl group having at least one ether bond on the main chain).

Still another aspect of the present invention is a method for producing a dithioglycoluril compound, the method comprising a first step of causing a reaction between formaldehyde and a compound of the following Formula (4b) in a basic aqueous solution, and then isolating a compound of the following Formula (3a); and a second step of causing a reaction between the compound of the following Formula (3a) and an alcohol of the following Formula (5) in an acidic solution containing the alcohol as a solvent, adding a basic aqueous solution to the resultant reaction mixture, and washing the resultant product with water for removal of impurities from the product, so as to produce to dithioglycoluril compound of the following Formula (3b):

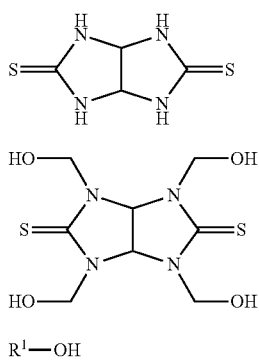

(4b)

(3a)

(5)

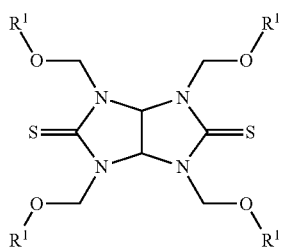

(3b)

(wherein four $R^1$s are each a linear, branched, or cyclic alkyl group having a carbon atom number of 1 to 4, a phenyl group, a naphthyl group, a benzyl group, or a $C_{3-9}$ alkyl group having at least one ether bond on the main chain).

Effects of the Invention

The thioglycoluril compound according to the present invention is produced by substitution of the hydrogen atoms bonded to the our nitrogen atoms of thioglycoluril with a —$Ch_2$—O—R group (wherein R has the same meaning as defined above in Formula (1)), and the compound is a novel sulfur-containing heterocyclic compound. A thioglycoluril compound having two or more —$CH_2$—O—R groups (wherein R has the same meaning as defined above) in the molecule is useful as, for example, a crosslinking agent for epoxy resins. In particular, 1,3,4,6-tetrakis(methoxymethyl)monothioglycoluril and 1,3,4,6-tetrakis(methoxymethyl)dithioglycoluril, in which the hydrogen atoms on all the nitrogen atoms are substituted with a methoxymethyl group, have excellent crosslinking performance.

1,3,4,6-Tetrakis(methoxymethyl)monothioglycoluril and 1,3,4,6-tetrakis(methoxymethyl)dithioglycoluril, which contain a sulfur atom, are expected to have optical properties different from those of 1,3,4,6-tetrakis(methoxymethyl)glycoluril. In particular, 1,3,4,6-tetrakis(methoxymethyl)monothioglycoluril has an asymmetric molecular structure and thus low molecular symmetry. Therefore, when used as, for example, a crosslinking agent for epoxy resins, 1,3,4,6-tetrakis(methoxymethyl)monothioglycoluril exhibits higher solubility in a solvent than conventional 1,3,4,6-tetrakis(methoxymethyl)glycoluril.

BRIEF DESCRIPTION OF THE DRAWINGS

FIG. 1 shows $^1$H-NMR spectra of 1,3,4,6-tetrakis(methoxymethyl)monothioglycoluril.

FIG. 2 shows $^1$H-NMR spectra of 1,3,4,6-tetrakis(methoxymethyl)dithioglycoluril.

FIG. 3 shows UV spectra of 1,3,4,6-tetrakis(methoxymethyl)glycoluril, 1,3,4,6-tetrakis(methoxymethyl)monothioglycoluril, and 1,3,4,6-tetrakis(methoxymethyl)dithioglycoluril.

MODES FOR CARRYING OUT THE INVENTION

The thioglycoluril compound of the present invention is a monothioglycoluril compound of the following Formula (2):

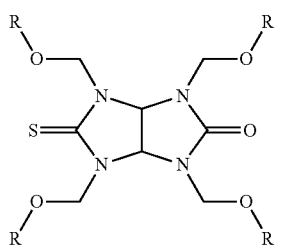

(2)

(wherein four Rs are each a hydrogen atom, a linear, branched, or cyclic alkyl group having a carbon atom number of 1 to 6, a phenyl group, a naphthyl group, a benzyl group, or a $C_{3-9}$ alkyl group having at least one ether bond on the main chain).

The thioglycoluril compound of the present invention is a dithioglycoluril compound of the following Formula (3):

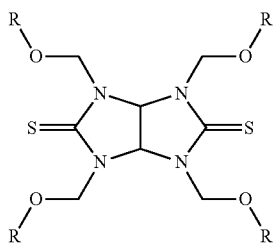

(3)

(wherein four Rs have the same meanings as defined above in Formula (2)).

In the monothioglycoluril compound of Formula (2) and the dithioglycoluril compound of Formula (3), when four Rs are each a linear, branched, or cyclic alkyl group, the number of carbon atoms of the alkyl group is, for example, 1 to 12, preferably 1 to 4, most preferably 1. Thus, the, most preferred alkyl group is a methyl group.

Preferred examples of monothioglycoluril compound and dithioglycoluril compound of the present invention wherein four Rs are each the aforementioned alkyl group include 1,3,4,6-tetrakis(methoxymethyl)monothioglycoluril, 1,3,4,6-tetrakis(ethoxymethyl)monothioglycoluril, 1,3,4,6-tetrakis(propoxymethyl)monothioglycoluril, 1,3,4,6-tetrakis(n-butoxymethyl)monothioglycoluril, 1,3,4,6-tetrakis(methoxymethyl)dithioglycoluril, 1,3,4,6-tetrakis(ethoxymethyl)dithioglycoluril, 1,3,4,6-tetrakis(propoxymethyl)dithioglycoluril, and 1,3,4,6-tetrakis(n-butoxymethyl)dithioglycoluril.

In the monothioglycoluril compound of Formula (2) and the dithioglycoluril compound of Forumla (3), when R is an alkyl group having at least one ether bond on the main chain, the number of carbon atoms of the alkyl group having at least one ether bond on the main chain is, for example, 3 to 9, preferably 3 to 5, most preferably 4.

Preferred examples of the monothioglycoluril compound and dithioglycoluril compound of the present invention wherein four Rs are each the aforementioned alkyl group having at least one ether bond on the main chain include 1,3,4,6-tetrakis((2-methoxyethoxy)methyl)monothioglycoluril, 1,3,4,6-tetrakis((2-(2-methoxyethoxy)ethoxy)methyl)monothioglycoluril, 1,3,4,6-tetrakis(((1-methoxypropan-2-yl)oxy)methyl)monothioglycoluril, 1,3,4,6-tetrakis(((1-ethoxypropan-2-yl)oxy)methyl)monothioglycoluril, 1,3,4,6-tetra(2,5,8,11-tetraoxadodecyl)monothioglycoluril, 1,3,4,6-tetra(2,5,8,11,14-pentaoxapentadecyl)monothioglycoluril, 1,3,4,6-tetrakis((2-methoxyethoxy)methyl)dithioglycoluril, 1,3,4,6-tetrakis((2-(2-methoxyethoxy)ethoxy)methyl)dithioglycoluril, 1,3,4,6-tetrakis(((1-methoxypropan-2-yl)oxy)methyl)dithioglycoluril, 1,3,4,6-tetrakis(((1-ethoxypropan-2-yl)oxy)methyl)dithioglycoluril, 1,3,4,6-tetra(2,5,8,11-tetraoxadodecyl)dithioglycoluril, and 1,3,4,6-tetra(2,5,8,11,14-pentaoxapentadecyl)dithioglycoluril.

A monothioglycoluril compound of the following Formula (2b):

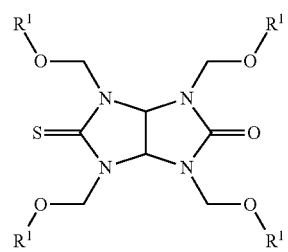

(2b)

(wherein four $R^1$s are each a linear, branched, or cyclic alkyl group having a carbon atom number of 1 to 6, a phenyl group, a naphthyl group, a benzyl group, or a $C_{3-9}$ alkyl group having at least one ether bond on the main chain) can be produced by reacting 1,3,4,6-tetramethylolmonothioglycoluril of the following Formula (2a):

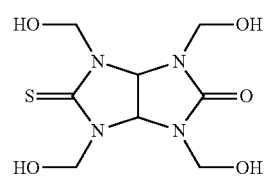

(2a)

with an alcohol, to thereby etherify the methylol groups of the 1,3,4,6-tetramethylolmonothioglycoluril.

A dithioglycoluril compound of the following Formula (3b):

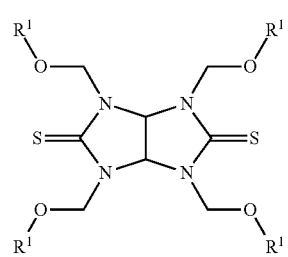

(3b)

(wherein four $R^1$s are each a linear, branched, or cyclic alkyl group having a carbon atom number of 1 to 6, a phenyl group, a naphthyl group, a benzyl group, or a $C_{3-9}$ alkyl group having at least one ether bond on the main chain) can be produced by reacting 1,3,4,6-tetramethyloldithioglycoluril of the following Formula (3a):

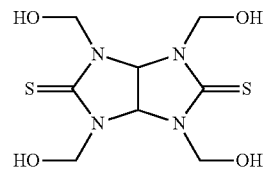

(3a)

with an alcohol, to thereby etherify the methylol groups of the 1,3,4,6-tetramethyloldithioglycoluril.

Methods of etherifying methylol group have been known, and any known method can be used in the present invention. The etherification method may be, for example, a method involving the use of an acid selected from the group consisting of hydrochloric acid, nitric acid, and sulfuric acid.

The acid is used in an amount of preferably 0.1 equivalents to 1.0 equivalent relative to a tetramethylolthioglycoluril compound.

The reaction solvent used for the aforementioned etherification is an alcohol of the following Formula (5):

$$R^1-OH \quad (5)$$

(wherein $R^1$ has the same meaning as defined above in Formulae (2b) and (3b)).

The reaction temperature for etherification of a tetramethylolthioglycoluril compound using any of the aforementioned acids may vary depending on the type of the reaction solvent used, and is generally 10° C. to 150° C. The reaction time must be varied with the reaction temperature, and is generally 1 hour to 4 hours.

After completion of the reaction, a base (e.g., an aqueous sodium hydroxide solution) is added to the resultant reaction mixture for adjustment of the pH thereof, and the resultant reaction product is concentrated, or dissolved in an appropriate solvent and separated by filtration, to thereby yield a product containing a monothioglycoluril or dithioglycoluril compound of interest.

The resultant product is subjected to washing with a solvent such as water, crystallization, or purification by, for example, silica gel column chromatography, to thereby remove impurities from the product.

1,3,4,6-Tetramethylolmonothioglycoluril of Formula (2a) can be produced by reacting monothioglycoluril of the following Formula (4a):

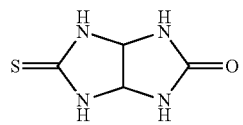
(4a)

with formaldehyde for methylolation of the hydrogen atoms bonded to the nitrogen atoms of the monothioglycoluril.

1,3,4,6-Tetramethyloldithioglycoluril of Formula (3a) can be produced by reacting dithioglycoluril of the following Formula (4b):

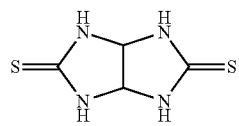
(4b)

with formaldehyde for methylolation of the hydrogen atoms bonded to the nitrogen atoms of the dithioglycoluril.

Methods of methylolation of a hydrogen atom bonded to a nitrogen atom have been known, and any known method can be used in the present invention. The methylolation method may be a method involving the use of, for example, a base selected from the group consisting of sodium hydroxide and potassium hydroxide in an aqueous formaldehyde solution. The base is used in an amount of preferably 0.001 equivalents to 0.01 equivalents relative to monothioglycoluril or dithioglycoluril.

The reaction solvent used for the aforementioned methylolation is water.

The reaction temperature for methylotation of a thioglycoluril compound using any of the aforementioned bases is 25° C. to 100° C. The reaction time must be varied with the reaction temperature, and is generally 1 hour to 24 hours.

EXAMPLES

The present invention will next be described by way of examples, but the present invention is not particularly limited to the examples.

Synthesis Example 1

Synthesis of Monothioglycoluril

Monothioglycoluril of Formula (4a) was synthesized according to the method described in Non-Patent Document 1: European Journal of Organic Chemistry, pp. 933-940 (2014).

Synthesis Example 2

Synthesis of Dithioglycoluril

Dithioglycoluril of Formula (4b) was synthesized according to the method described in Non-Patent Document 4: Tetrahedron Letters, 56, 6085-6088 (2015).

Example 1

Synthesis of 1,3,4,6-Tetramethylolmonothioglycoluril

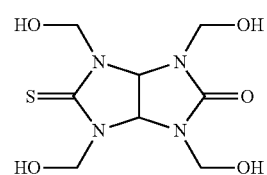
(2a)

To a 50 mL flask equipped with a cooler, a thermometer, and a stirrer, 12.84 g (158.0 mmol) of 37% by mass aqueous formaldehyde solution (available from Tokyo Chemical Industry Co., Ltd.) and 0.38 g (7.7 mmol) of 0.5 N aqueous sodium hydroxide solution were added, and the mixture was heated to 40° C. and stirred. At the same temperature, 5.00 g (31.6 mmol) of monothioglycoluril obtained in Synthesis Example 1 was added to the flask, and the mixture was heated to 55° C. and stirred for five hours. The mixture was then cooled to 25° C., and 0.09 g (1.8 mmol) of 0.5 N aqueous sodium hydroxide solution was added to the mixture, followed by stirring. Thereafter, 25.00 g of methanol was added to the mixture, and the mixture was stirred at 5° C., to thereby precipitate crystals. The precipitated crystals were filtered and washed with 5.00 g of methanol twice. The resultant residue was dried under reduced pressure, to thereby produce 6.27 g of 1,3,4,6-tetramethylolmonothioglycoluril of Formula (2a) as a white solid. The yield was 71.3%, and the purity was 100% as determined by high-performance liquid chromatography (hereinafter abbreviated as "HPLC").

The produced 1,3,4,6-tetramethylolmonothioglycoluril showed δ values of $^1$H-NMR spectra (DMSO-$d_6$) as follows.

δ: 6.06 (dd, 4H), 5.72 (s, 2H), 5.19 (dd, 2H), 5.12 (dd, 2H), 4.84 (dd, 2H), 4.72 (dd, 2H).

Example 2

Synthesis of
1,3,4,6-Tetrakis(methoxymethyl)monothioglycoluril

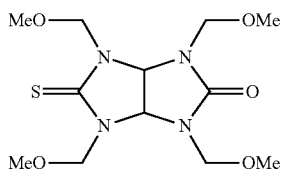
(2b-1)

To a 50 mL flask equipped with a cooler, a thermometer, and a stirrer, 3.00 g (10.8 mmol) of 1,3,4,6-tetramethylolmonothioglycoluril produced in Example 1, 6.91 g of methanol, and 0.23 g (2.4 mmol) of 65% by mass nitric acid were added, and the mixture was heated to 40° C. and stirred for 25 hours. Thereafter, the mixture was cooled to 25° C., and 0.49 g (2.4 mmol) of 20% by mass aqueous sodium hydroxide solution was added to the mixture. The solvent was distilled off under reduced pressure at 40° C. To the resultant concentrate, 30.00 g of ethyl acetate was added. The mixture was filtered and washed with 3.00 g of ethyl acetate twice, and the solvent was distilled off under reduced pressure. The resultant residue was purified by silica gel column chromatography (ethyl acetate/n-heptane=3/1 (by volume)), to thereby produce 2.39 g of 1,3,4,6-tetrakis(methoxymethyl)monothioglycoluril of Formula (2b-1) as a white solid. The yield was 66.4%, and the purity was 100% as determined by HPLC.

FIG. 1 shows $^1$H-NMR spectra oldie produced 1,3,4,6-tetrakis(methoxymethyl)monothioglycoluril. The δ values of the NMR spectra (DMSO-$d_6$ were as follows.

δ: 5.74 (s, 2H), 5.21 (d, 2H), 5.11 (d, 2H), 4.75 (d, 2H), 4.71 (d, 2H), 3.26 (s, 6H), 3.20 (s, 6H).

Example 3

Synthesis of 1,3,4,6-Tetramethyloldithioglycoluril

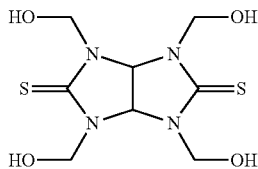
(3a)

To a 50 mL flask equipped with a cooler, a thermometer, and a stirrer, 0.70 g (8.6 mmol) of 37% by mass aqueous formaldehyde solution (available from Tokyo Chemical Industry Co., Ltd.), 0.023 g (0.46 mmol) of 0.5 N aqueous sodium hydroxide solution, and 1.50 g of water were added, and the mixture was heated to 40° C. and stirred. At the same temperature, 0.30 g (1.7 mmol) of dithioglycoluril obtained in Synthesis Example 2 was added to the flask, and the mixture was heated to 55° C. and stirred for one hour. Thereafter, the mixture was cooled to 25° C., and 1.50 g of methanol was added to the mixture, to thereby precipitate crystals. The precipitated crystals were filtered and washed with 0.60 g of methanol twice. The resultant residue was dried under reduced pressure, to thereby produce 0.30 g of 1,3,4,6-tetramethyloldithioglycoluril of Formula (3a) as a white solid. The yield was 59.6%, and the purity was 100% as determined by HPLC.

The produced 1,3,4,6-tetramethyloldithioglycoluril showed δ values of $^1$H-NMR spectra (DMSO-$d_6$) as follows.

δ: 6.18 (t, 4H), 5.95 (s, 2H), 5.18 (d, 8H).

Example 4

Synthesis of
1,3,4,6-Tetrakis(methoxymethyl)dithioglycoluril

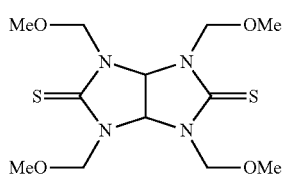
(3b-1)

To a 50 mL flask equipped with a cooler, a thermometer, and a stirrer, 0.29 g (1.0 mmol) of 1,3,4,6-tetramethyloldithioglycoluril produced in Example 3, 1.32 g (41.2 mmol) of methanol, and 0.049 g (0.5 mmol) of 65% by mass nitric acid were added, and the mixture was heated to 40° C. and stirred for 34 hours. Thereafter, the mixture was cooled to 25° C., and 0.14 g (0.7 mmol) of 20% by mass aqueous sodium hydroxide solution was added to the mixture. The solvent was distilled off under reduced pressure at 40° C. To the resultant concentrate, 2.6 g of pure water was added, to thereby precipitate crystals. The precipitated crystals were filtered and washed with 1.3 g of pure water twice. The resultant residue was dried under reduced pressure, to thereby produce 0.13 g of 1,3,4,6-tetrakis(methoxymethyl)monothioglycoluril of Formula (3b-1) as a white solid. The yield was 36.9%, and the purity was 97.1% as determined by HPLC.

FIG. 2 shows $^1$H-NMR spectra of the produced 1,3,4,6-tetrakis(methoxymethyl)dithioglycoluril. The δ values of the NMR spectra (DMSO-$d_6$) were as follows.

δ: 5.98 (s, 2H), 5.21 (d, 4H), 5.15 (d, 4H), 3.27 (s, 12H).

FIG. 3 shows UV spectra of 1,3,4,6-tetrakis(methoxymethyl)monothioglycoluril (hereinafter abbreviated as "TMOM-TGU") produced in Example 2, 1,3,4,6-tetrakis(methoxymethyl)dithioglycoluril (hereinafter abbreviated as "TMOM-DTGU") produced in Example 4, and commercially available 1,3,4,6-tetrakis(methoxymethyl)glycoluril (product name: POWDERLINK1174, hereinafter abbreviated as "TMOM-GU") as Comparative Example.

As is clear from the results shown in FIG. 3, the thioglycoluril compound according to the present invention exhibits a shift of UV absorption wavelength as compared with the sulfur atom-free glycoluril, and has UV absorption around 248 nm.

In order to examine the solubilities of TMOM-TGU produced in Example 2, TMOM-DTGU produced in Example 4, and TMOM-GU as Comparative Example, these compounds were dissolved in propylene glycol 1-monomethyl ether (PGME) or propylene glycol 1-monomethyl ether 2-acetate (PGMEA), each of which is a solvent commonly used in, for example, production processes for semiconductor devices. The results are shown in Table 1.

As is clear from the results shown in Table 1, 1,3,4,6-tetrakis(methoxymethyl)monothioglycoluril exhibits particularly excellent solubility in a solvent, since it has an asymmetric molecular structure and thus low molecular symmetry.

TABLE 1

| | Examples | | Comparative Example |
|---|---|---|---|
| | TMOM-TGU | TMOM-DTGU | TMOM-GU |
| | (structure) | (structure) | (structure) |
| Solubility (g/100 g-PGME) | 100 | 20 | 20 |
| Solubility (g/100 g-PGMEA) | 100 | 25 | 12.5 |

INDUSTRIAL APPLICABILITY

The thioglycoluril compound according to the present invention is expected to be useful as, for example, a crosslinking agent for epoxy resins. In addition, the thioglycoluril compound according to the present invention has absorption at the wavelength of KrF eximer laser and thus is useful as a crosslinking agent for an anti-reflective coating-forming composition.

The invention claimed is:

1. A thioglycoluril compound of the following Formula (1):

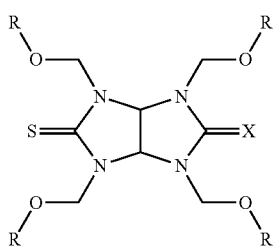

(1)

(wherein X is an oxygen atom or a sulfur atom, and four Rs are each a hydrogen atom, a linear, branched, or cyclic alkyl group having a carbon atom number of 1 to 4, a phenyl group, a naphthyl group, a benzyl group, or a $C_{3-9}$ alkyl group having at least one ether bond on the main chain).

2. The thioglycoluril compound according to claim 1, wherein the thioglycoluril compound is a monothioglycoluril compound of the following Formula (2):

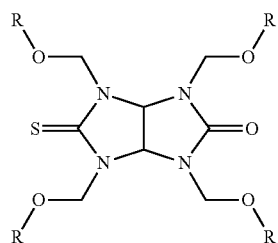

(2)

(wherein four Rs have the same meanings as defined above in Formula (1)).

3. The thioglycoluril compound according to claim 1, wherein the thioglycoluril compound is a dithioglycoluril compound of the following Formula (3):

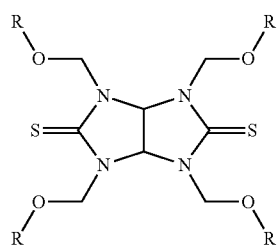

(3)

(wherein four Rs have the same meanings as defined above in Formula (1)).

* * * * *